(12) United States Patent
Shin et al.

(10) Patent No.: US 9,770,740 B2
(45) Date of Patent: Sep. 26, 2017

(54) ULTRASONIC TRANSDUCER AND ULTRASONIC DIAGNOSTIC APPARATUS INCLUDING THE SAME

(71) Applicant: SAMSUNG ELECTRONICS CO., LTD., Suwon-si (KR)

(72) Inventors: Hyung-jae Shin, Seongnam-si (KR); Sang-ha Park, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 643 days.

(21) Appl. No.: 14/276,051

(22) Filed: May 13, 2014

(65) Prior Publication Data

US 2015/0107362 A1    Apr. 23, 2015

(30) Foreign Application Priority Data

Oct. 23, 2013    (KR) .................. 10-2013-0126701

(51) Int. Cl.
*B06B 1/02* (2006.01)
*G01N 29/26* (2006.01)
*B06B 1/06* (2006.01)
*A61B 8/00* (2006.01)

(52) U.S. Cl.
CPC .......... *B06B 1/0292* (2013.01); *A61B 8/4494* (2013.01); *B06B 1/0629* (2013.01); *G01N 29/26* (2013.01)

(58) Field of Classification Search
CPC . B06B 1/0292; B06B 1/0629; A61L 38/4494; G01N 29/26

USPC .......................................................... 73/641
See application file for complete search history.

(56) References Cited

U.S. PATENT DOCUMENTS

| 5,160,870 | A * | 11/1992 | Carson | B06B 1/0629 310/324 |
| 6,262,946 | B1 * | 7/2001 | Khuri-Yakub | G10K 11/002 367/153 |
| 6,328,696 | B1 * | 12/2001 | Fraser | B06B 1/0292 367/118 |
| 6,430,109 | B1 * | 8/2002 | Khuri-Yakub | B06B 1/0292 367/181 |

(Continued)

FOREIGN PATENT DOCUMENTS

| JP | 2004-33666 A | 2/2004 |
| JP | 4017934 B2 | 12/2007 |
| KR | 10-2012-0047599 A | 5/2012 |

*Primary Examiner* — Lisa Caputo
*Assistant Examiner* — Nathaniel T Woodward
(74) *Attorney, Agent, or Firm* — Sughrue Mion, PLLC (57) ABSTRACT

An ultrasonic transducer and ultrasonic diagnostic apparatus are provided. An ultrasonic transducer includes a substrate including a trench formed in a lower surface of the substrate; and a first element and a second element formed on an upper surface of the substrate and are located adjacent to each other, wherein the trench is positioned between the first element and the second element, wherein the first element and the second element each include a plurality of ultrasonic cells that are two-dimensionally arranged; wherein a first contour line of the first element and a second contour line of the second element, which are adjacent to each other, each form a zig-zag line which are complementary with each other, and the trench is formed in a zig-zag pattern between the first contour line and the second contour line.

18 Claims, 8 Drawing Sheets

(56) References Cited

U.S. PATENT DOCUMENTS

| | | | | |
|---|---|---|---|---|
| 6,669,644 | B2* | 12/2003 | Miller | G10K 11/002 367/181 |
| 7,411,260 | B2* | 8/2008 | Enomoto | H01L 29/84 257/414 |
| 7,736,985 | B2* | 6/2010 | Enomoto | G01S 7/52079 257/416 |
| 8,033,997 | B2* | 10/2011 | Fiasca | G01S 7/52047 600/407 |
| 8,099,854 | B2* | 1/2012 | Kato | H04R 31/00 29/594 |
| 2004/0190377 | A1* | 9/2004 | Lewandowski | B06B 1/0292 367/174 |
| 2007/0228878 | A1* | 10/2007 | Huang | B06B 1/0238 310/322 |
| 2008/0259725 | A1* | 10/2008 | Bayram | B06B 1/0292 367/7 |
| 2010/0265159 | A1* | 10/2010 | Ando | H01Q 9/0421 343/913 |
| 2012/0319535 | A1* | 12/2012 | Dausch | B06B 1/0622 310/365 |
| 2012/0319802 | A1* | 12/2012 | Ochiai | H03H 9/1092 333/193 |

* cited by examiner

ULTRASONIC TRANSDUCER AND ULTRASONIC DIAGNOSTIC APPARATUS INCLUDING THE SAME

CROSS-REFERENCE TO RELATED APPLICATION

This application claims priority from Korean Patent Application No. 10-2013-0126701, filed on Oct. 23, 2013, in the Korean Intellectual Property Office, the disclosure of which is incorporated herein in its entirety by reference.

BACKGROUND

1. Field

Apparatuses consistent with the exemplary embodiments relate to ultrasonic transducers capable of generating and detecting an ultrasonic wave and ultrasonic diagnostic apparatuses including the ultrasonic transducer.

2. Description of the Related Art

An ultrasonic diagnostic apparatus irradiates an ultrasonic wave onto an internal part of an object, such as an organ of a human being or an animal, and detects an echo signal which is reflected from the internal part of the object. The ultrasonic diagnostic apparatus can then display a cross-sectional image of an organ in the object and provide information that is necessary to diagnose a disease in the object.

A probe in the ultrasonic diagnostic apparatus includes an ultrasonic transducer for converting an electric signal into an ultrasonic signal, or vice versa. The ultrasonic transducer has a plurality of ultrasonic cells that are arranged two-dimensionally. Micromachined ultrasonic transducers (MUTs) have been adopted as the ultrasonic cells. An MUT may be classified as a piezoelectric MUT (pMUT), a capacitive MUT (cMUT), and a magnetic MUT (mMUT) according to a conversion type thereof.

SUMMARY

One or more exemplary embodiments provide an ultrasonic transducer capable of increasing an effective area for generating and/or sensing ultrasonic waves, and an ultrasonic diagnostic apparatus employing the ultrasonic transducer.

One or more exemplary embodiments provide an ultrasonic transducer capable of reducing the amount of a decrease in a bandwidth of a frequency response property, and an ultrasonic diagnostic apparatus employing the ultrasonic transducers.

Additional aspects will be set forth in part in the description which follows and, in part, will be apparent from the description, or may be learned by practice of the presented exemplary embodiments.

According to an aspect of an exemplary embodiment, an ultrasonic transducer includes a substrate including a trench formed in a lower surface of the substrate, and a first element and a second element formed on an upper surface of the substrate and are located adjacent to each other, wherein the trench is positioned between the first element and the second element, wherein the first element and the second element each include a plurality of ultrasonic cells that are two-dimensionally arranged, wherein a first contour line of the first element and a second contour line of the second element, which are adjacent to each other, each form a zig-zag line which are complementary with each other, and the trench is formed in a zig-zag pattern between the first contour line and the second contour line.

The first contour line may be a line configured to connect edges of a plurality of first ultrasonic cells adjacent to the trench from among the plurality of ultrasonic cells in the first element, and the second contour line may be a line connecting edges of a plurality of second ultrasonic cells adjacent to the trench from among the plurality of ultrasonic cells in the second element.

The plurality of first ultrasonic cells and the plurality of second ultrasonic cells may not overlap with each other.

An effective gap between a first ultrasonic cell located closest to the second element from among the plurality of first ultrasonic cells and a second ultrasonic cell located closest to the first element from among the plurality of second ultrasonic cells, and wherein a size of the effective gap may be equal to or greater than a size of a cell gap between the plurality of ultrasonic cells among the plurality of ultrasonic cells in the first element and the second element.

The plurality of ultrasonic cells in the first element may be hexagonally arranged, and the plurality of ultrasonic cells in the second element may be hexagonally arranged with respect to the plurality of ultrasonic cells in the first element.

Each of the plurality of ultrasonic cells may be a capacitive micromachined ultrasonic transducer (cMUT).

According to an aspect of an exemplary embodiment, an ultrasonic transducer includes a substrate, a first element including a first plurality of ultrasonic cells hexagonally arranged on an upper surface of the substrate, and a second element adjacent to the first element and including a second plurality of ultrasonic cells hexagonally arranged with respect to the first element, wherein a plurality of first ultrasonic cells located at an edge portion of the first element, which is adjacent to the second element, and a plurality of second ultrasonic cells located at an edge portion of the second element, which is adjacent to the first element, are arranged in a zig-zag pattern.

A trench configured to block a transmission of a bulk acoustic wave between the first element and the second element may be formed in the substrate, and wherein the trench may be formed in a zig-zag pattern between the plurality of first ultrasonic cells and the plurality of second ultrasonic cells.

The trench may be located on a lower surface of the substrate.

An effective gap between a first ultrasonic cell located closest to the second element from among the plurality of first ultrasonic cells and a second ultrasonic cell located closest to the first element from among the plurality of second ultrasonic cells, and wherein a size of the effective gap may be equal to or greater than a size of cell gap between the plurality of ultrasonic cells among the plurality of ultrasonic cells in the first element and the second element.

Each of the plurality of ultrasonic cells may be a capacitive micromachined ultrasonic transducer (cMUT).

According to an aspect of an exemplary embodiment, an ultrasonic diagnostic apparatus includes an ultrasonic probe comprising an ultrasonic transducer, and configured to transmit an ultrasonic wave toward an object and configured to receive an ultrasonic wave reflected by the object to generate an echo signal which includes information about the object, and a signal processing device configured to generate images of the object based on the echo signal.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Reference will now be made in detail with respect to exemplary embodiments, examples of which are illustrated in the accompanying drawings. Like reference numerals refer to the like elements throughout. In this regard, the exemplary embodiments may have different forms and should not be construed as being limited to the descriptions set forth herein. Accordingly, the exemplary embodiments are merely described below, by referring to the figures, to explain aspects of the present description.

Figure 1:
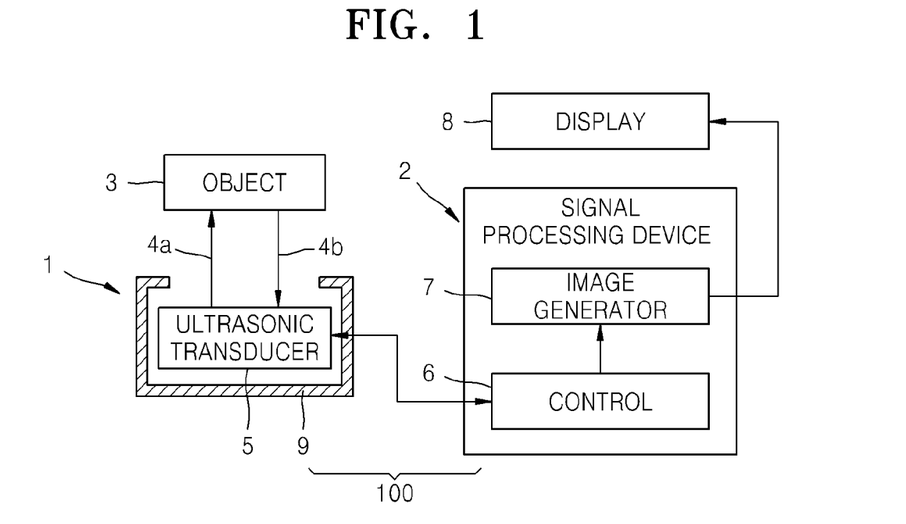
FIG. 1 is a schematic block diagram of an ultrasonic diagnostic apparatus according to an exemplary embodiment.

FIG. 1 is a schematic block diagram of an ultrasonic diagnostic apparatus. Referring to FIG. 1, the ultrasonic diagnostic apparatus 100 includes an ultrasonic probe 1 and a signal processing device 2. The ultrasonic probe 1 includes an ultrasonic transducer 5 that transmits an ultrasonic wave 4a toward an object 3. The object 3 can be, for example, a human body or part of a human body. The object 3 receives an ultrasonic wave 4b reflected from the object 3. The ultrasonic transducer 5 is accommodated in a housing 9.

The signal processing device 2 controls the ultrasonic probe 1 and generates an image of the object 3, based on an echo signal representing information about the object 3, which is detected by the ultrasonic probe 1. The signal processing device 2 may include a control 6 and an image generator 7. The control 6 may control the ultrasonic transducer 5 so as to transmit and/or receive the ultrasonic waves 4a and 4b. The control 6 determines a location where the ultrasonic wave is to be irradiated and an intensity of the irradiated ultrasonic wave, and controls the ultrasonic transducer 5 according to the determination. One of ordinary skill in the art would appreciate that the control 6 may additionally control general operations of the ultrasonic probe 1.

The ultrasonic transducer 5 may receive an echo ultrasonic wave reflected from the object 3 to generate an echo signal in order to perform the diagnosis. The image generator 7 receives the echo signal, and generates ultrasonic images of the object by using the echo signal. The processes of generating the ultrasonic images by using the echo signal are well known in the art, and thus, detailed descriptions thereof are omitted here.

The ultrasonic images may be displayed on a display 8. The display 8 could be for example, a monitor.

The signal processing device 2 may be realized by, for example, a processor including an array of a plurality of logic gates, or may be realized as a combination of a universal microprocessor and a memory storing a program that may be executed in the microprocessor. In addition, one of ordinary skill in the art would appreciate that the signal processing device 2 may be realized as an appropriate type of hardware.

Figure 2:
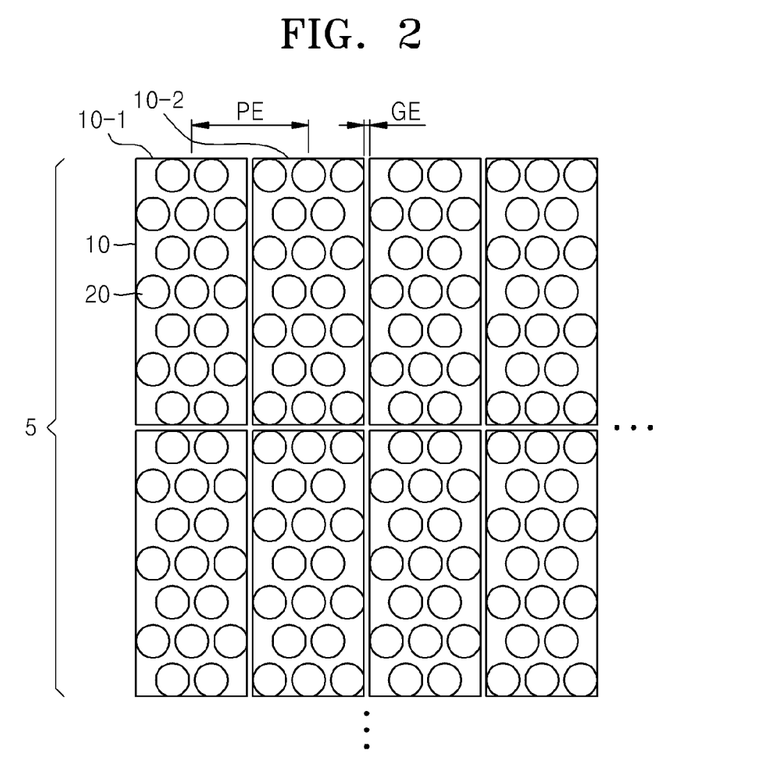
FIG. 2 is a plan view of the ultrasonic transducer according to an exemplary embodiment.

FIG. 2 is a plan view of the ultrasonic transducer 5 according to the exemplary embodiment. Referring to FIG. 2, the ultrasonic transducer 5 includes a plurality of elements 10 that are arranged two-dimensionally in a lateral direction and in an elevation direction. The elements 10 can be, for example, transducing elements. Each of the elements 10 includes a plurality of ultrasonic cells 20 arranged two-dimensionally. Each of the ultrasonic cells 20 acts as an ultrasonic transducer by itself, and the ultrasonic cell 20 may be, for example, a piezoelectric micromachined ultrasonic transducer (pMUT), a capacitive micromachined ultrasonic transducer (cMUT), or a magnetic micromachined ultrasonic transducer (mMUT).

In the present exemplary embodiment, the cMUT is adopted as the ultrasonic cells 20. Since the pMUT uses a piezoelectric device, there are often limitations in manufacturing a fine MUT. The cMUT has a size of about tens of microns. Since the cMUT may be formed by a series of semiconductor manufacturing processes, more ultrasonic cells 20 may be arranged two-dimensionally in a restricted area when a cMUT is adopted as an ultrasonic cell 20 as opposed to when a pMUT is adopted as an ultrasonic cell 20. Thus, a high level of diagnostic accuracy may be achieved, and a high resolution diagnostic image may be obtained.

Figure 3:
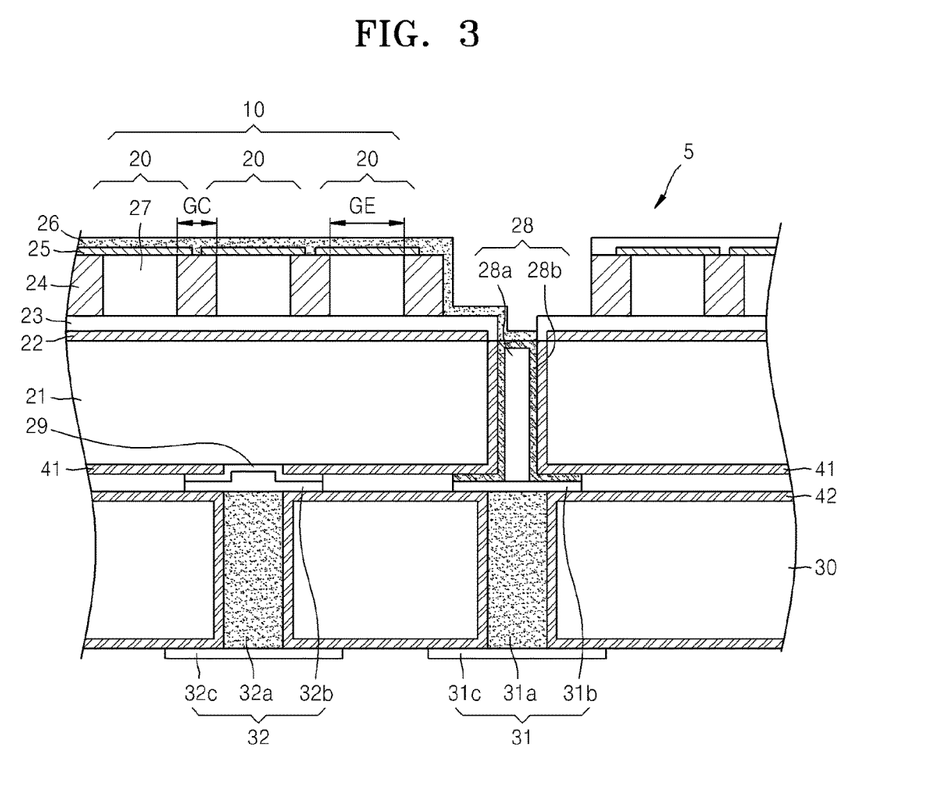
FIG. 3 is a cross-sectional view of a capacitive micromachined ultrasonic transducer (cMUT) as an example of an ultrasonic cell, according to an exemplary embodiment.

FIG. 3 is a cross-sectional view of an ultrasonic transducer 5 adopting a cMUT as the ultrasonic cell 20. Referring to FIG. 3, the cMUT may be manufactured by forming a lower electrode 22, an insulating layer 23, and a wall body 24 for defining a cavity 27, on a substrate 21, and providing a vibration layer 25, on which an upper electrode 26 is formed, on the wall body 24. Since the substrate 21 may act as the lower electrode 22 when the substrate 21 is a low resistive substrate, the lower electrode 22 shown in FIG. 3 may be omitted.

According to the above configuration, the lower electrode 22 and the vibration layer 25, on which the upper electrode 26 is located, form a capacitor. When a direct current (DC) voltage is applied between the lower electrode 22 and the upper electrode 26, the vibration layer 25 is displaced by an electrostatic force, such as a Coulomb force. That is, the vibration layer 25 is pulled down to the lower electrode 22. The vibration layer 25 is stopped at a location where drag caused by an internal stress of the vibration layer 25 and the electrostatic force are balanced. In this state, when an alternating current (AC) voltage that is less than the DC voltage is applied between the lower electrode 22 and the upper electrode 26, the vibration layer 25 vibrates to generate ultrasonic waves. On the contrary, in a state where the vibration layer 25 is displaced due to the application of the DC voltage, when a sound pressure of an ultrasonic wave is applied to the vibration layer 25 from outside of the cMUT, displacement of the vibration layer 25 is changed. Variations in the displacement of the vibration layer 25 causes variations in electrostatic capacitance. By detecting the variation in the electrostatic capacitance, the ultrasonic wave may be received. That is, the ultrasonic wave used to perform a treatment and/or a diagnosis may be generated and received by using the cMUT.

The ultrasonic transducer 5 includes a plurality of elements 10, each forming one driving unit, arranged one-dimensionally or two-dimensionally, based on a required frequency performance, physical characteristics of a material, and limitations in the manufacturing processes. Each of the plurality of elements 10 includes a plurality of ultrasonic cells 20.

The substrate 21 on which the ultrasonic cells 20 are formed is disposed on a driving substrate 30. The driving substrate 30 includes a first power supply unit 31 and a second power supply unit 32 that are electrically connected to the upper electrode 26 and the lower electrode 22, respectively. Signal voltages may be applied to the ultrasonic cells 20, or ultrasonic sensing signals of the ultrasonic cells 20 may be received via path the first power supply unit 31 and the second power supply unit 32. In FIG. 3, reference numerals 41 and 42 denote insulating layers formed on the substrate 21 and the driving substrate 30.

The first power supply unit 31 includes a conductive via path 31a penetrating through the driving substrate 30 and filled with a conductive material therein, a conductive pad 31b located on an upper end portion of the conductive via path 31a, and an electrode pad 31c located at a lower portion of the conductive via path 31a for electrically connecting an external signal source and the conductive via path 31a to each other.

A first connection unit 28 for electrically connecting the upper electrode 26 and the first power supply unit 31 to each other may be disposed on the substrate 21. The first connection unit 28 may include a via hole 28a penetrating through the substrate 21, and a conductive layer 28b disposed in the via hole 28a and electrically connected to the upper electrode 26. A lower end portion of the conductive layer 28b may extend along a lower surface of the substrate 21, and may be electrically connected to the conductive pad 31b.

According to the above configuration, a voltage may be applied to the upper electrode 26 via the first power supply unit 31. The upper electrodes 26 on the ultrasonic cells 20 in one element 10 may form a common electrode. Otherwise, the upper electrodes 26 of all of the elements 10 configuring the ultrasonic transducer 5 may form a common electrode. However, one or more exemplary embodiments are not limited thereto, for example, the plurality of elements 10 may be classified as two or more groups, and a first power supply unit 31 may be formed with respect to each of the groups.

The second power supply unit 32 may include a conductive via path 32a penetrating through the driving substrate 30 and filled with a conductive material therein, a conductive pad 32b located on an upper end portion of the conductive via path 32a, and an electrode pad 32c disposed at a lower portion of the conductive via path 32a for electrically connecting the external signal source and the conductive via path 32a to each other. The substrate 21 may be a low resistive substrate. In this case, a structure for electrically connecting the lower electrode 22 to the second power supply unit 32 may be simplified.

Referring to FIG. 3, a second connection unit 29 that is electrically connected to the substrate 21 is disposed on a lower surface of the substrate 21. The second connection unit 29 may be a connection pad formed of a conductive material. The second connection unit 29 is connected to the conductive pad 32b. According to the above configuration, the second power supply unit 32 may apply an electric signal, for example, a voltage, to the lower electrode 22 from the external signal source, and may transfer a variation in electrostatic capacitance in the cavity 27 outside of the cMUT as an electric signal.

As described above, when the substrate 21 is a low resistive substrate, the substrate 21 may act as the lower electrode, and the lower electrode 22 may be omitted. In addition, although not shown in FIG. 3, if the substrate 21 is a highly resistive substrate, the second connection unit 29 may include a via hole penetrating through the substrate 21, and a conductive layer may be disposed in the via hole and electrically connected to the lower electrode 22 and the conductive pad 32b because a lower end portion of the conductive layer extends along the lower surface of the substrate 21.

The ultrasonic cells 20 in each of the elements 10 are separated from each other with cell gaps GC therebetween. An effective area of one ultrasonic cell 20 is equal to a projecting area of the cavity 27 on which the vibration layer 25 is disposed. Therefore, when the cell gap GC increases, an effective area ratio, that is, a ratio between an area of the element 10 and a total sum of the effective areas of the ultrasonic cells 20 that contribute to generate and/or sense the ultrasonic wave, is reduced. Thus, in the element 10, the ultrasonic cells 20 need to be arranged so as to maintain a relatively large effective area ratio.

Figure 4:
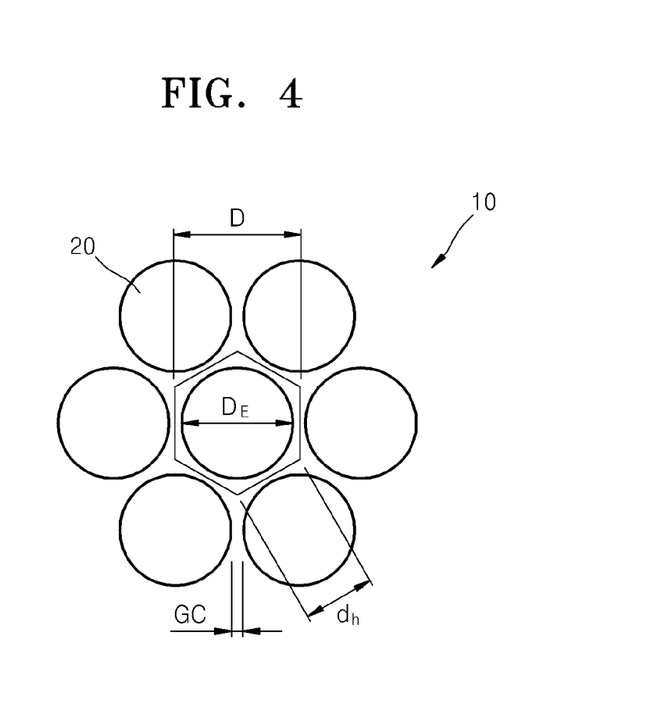
FIG. 4 is a plan view showing ultrasonic cells arranged hexagonally in an element, according to an exemplary embodiment.

According to the exemplary embodiment, the ultrasonic cells 20 in each of the elements 10 are hexagonally arranged. FIG. 4 shows an example of the ultrasonic cells 20 that are hexagonally arranged. According to the arrangement, a physical area occupied by each of the ultrasonic cells 20 in the element 10 is a regular hexagon, a side of which has a length of $d_h$, in consideration of the cell gaps GC between the ultrasonic cells 20. This regular hexagon circumscribes a circle, a diameter D of which is equal to an effective diameter $D_E$ of the ultrasonic cell 20+the cell gap GC, and in this case, an equation $D = \tan 60° \times d_h$ may be established.

An area Au occupied by the ultrasonic cell 20 is an area of the regular hexagon, a side of which has a length of $d_h$, and may be calculated by the following Equation 1.

$$A_u = \frac{6}{2}\tan 60° \times d_h^2 = \frac{6}{4}\frac{D^2}{\tan 60°} \quad \text{[Equation 1]}$$

When an effective radius of the ultrasonic cell 20 is $r = D_E/2$, an effective area $A_e$ of the ultrasonic cell 20 is $\pi r^2$, and thus, the effective area ratio of one ultrasonic cell 20 in the element 10 may be calculated by the following Equation 2.

$$\frac{A_e}{A_u} = \frac{4}{6}\tan 60° \frac{\pi r^2}{D^2} = 1.1547\frac{\pi r^2}{D^2} \quad \text{[Equation 2]}$$

Figure 5:
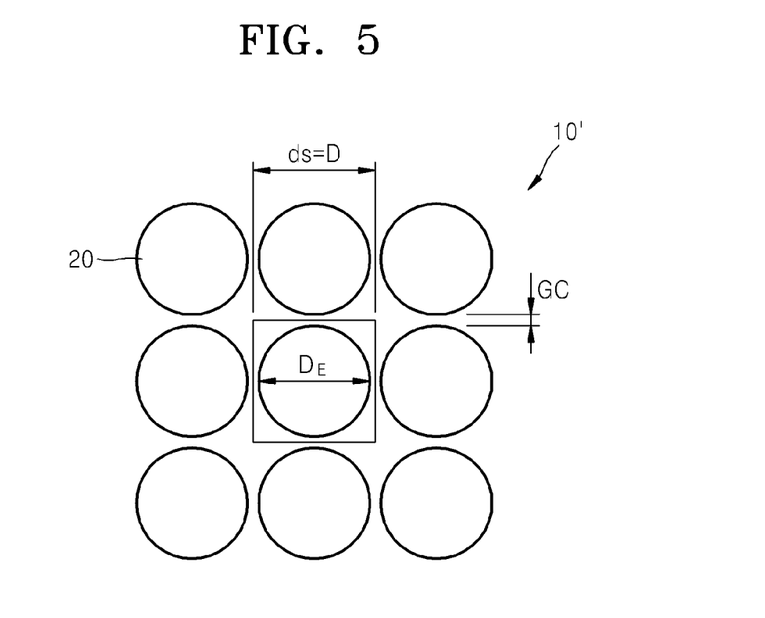
FIG. 5 is a plan view showing ultrasonic cells arranged as a square in an element, according to a comparative example.

As a comparative example, FIG. 5 shows an example of a square arrangement of the ultrasonic cells 20 in an element 10'. Here, an area occupied by one ultrasonic cell 20 in the element 10' is an area of a rectangle, a side of which has a length of ds, that is, $A_u' = ds^2 = D^2$. In addition, since the effective area of the ultrasonic cell 20 is $\pi r^2$, an effective area ratio of the ultrasonic cell 20 in the element 10' may be calculated by the following Equation 3.

$$\frac{A_e'}{A_u'} = \frac{\pi r^2}{D^2} \quad \text{[Equation 3]}$$

When comparing Equation 2 and the Equation 3 with each other, the effective area in a case of the hexagonal arrangement may be greater than that of the square arrangement by about 15.5%. This denotes that when the ultrasonic cells 20 having the effective areas $A_e$ are arranged hexagonally, more ultrasonic cells 20 may be arranged in a given area than when arranged in the square arrangement. Therefore, by arranging the ultrasonic cells 20 hexagonally, the effective area ratio of the ultrasonic cells 20 in the element 10 may be increased, thereby improving an ultrasonic wave generation efficiency and a sensitivity with respect to the ultrasonic wave.

Figure 6:
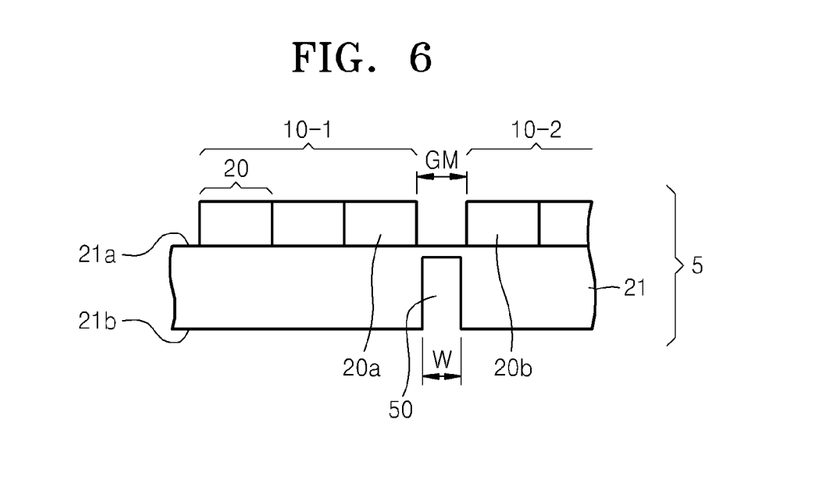
FIG. 6 is a cross-sectional view of an ultrasonic transducer in which a trench is formed between a first element and a second element that are adjacent to each other, according to an exemplary embodiment.

FIG. 6 is a schematic cross-sectional view of the ultrasonic transducer 5, in which a trench 50 is formed between two adjacent elements, that is, a first element 10-1 and a second element 10-2. FIG. 6 t shows the ultrasonic cells 20, and the driving substrate 30 is omitted. Referring to FIG. 6, the trench 50 may be formed in the substrate 21 in order to block the transmission of a bulk acoustic wave between the first element 10-1 and the second element 10-2 that are adjacent to each other. By blocking the bulk acoustic wave, crosstalk between the ultrasonic wave sensing signals of the first element 10-1 and the second element 10-2 may be prevented, thereby improving the sensitivity of the ultrasonic transducer 5.

The trench 50 extends from a lower surface 21b of the substrate 21 toward an upper surface 21a on which the ultrasonic cells 20 are arranged. A gap GM that is at least equal to a width W of the trench 50 or greater has to be maintained between a first ultrasonic cell 20a and a second ultrasonic cell 20b located at edge portions of the first element 10-1 and the second element 10-2. The width W of the trench 50 is determined by elements such as a material forming the substrate 21, in addition to limitations in the manufacturing processes of the ultrasonic transducer 5. Further, the width W of the trench 50 rarely changes even when a pitch PE (refer to FIG. 2) between the first element 10-1 and the second element 10-2 is changed. For example, in a case of an ultrasonic transducer for an abdomen, which is driven by a low frequency range, the pitch PE between the first element 10-1 and the second element 10-2 is about 250 µm. In a case of an ultrasonic transducer for a breast, which is driven by a high frequency range, the pitch PE between the first element 10-1 and the second element 10-2 is about 200 µm. However, since the width W of the trench 50 is not changed in both of the above cases, the gap GM has to be maintained between the first ultrasonic cell 20a and the second ultrasonic cell 20b that are located at edge portions of the first element 10-1 and the second element 10-2.

Although not shown in FIG. 6, the trench 50 may be formed between two elements 10 that are adjacent to each other in a vertical direction, and the trench 50 formed between the two elements 10 adjacent to each other in the vertical direction may be formed as a straight line.

Figure 7:
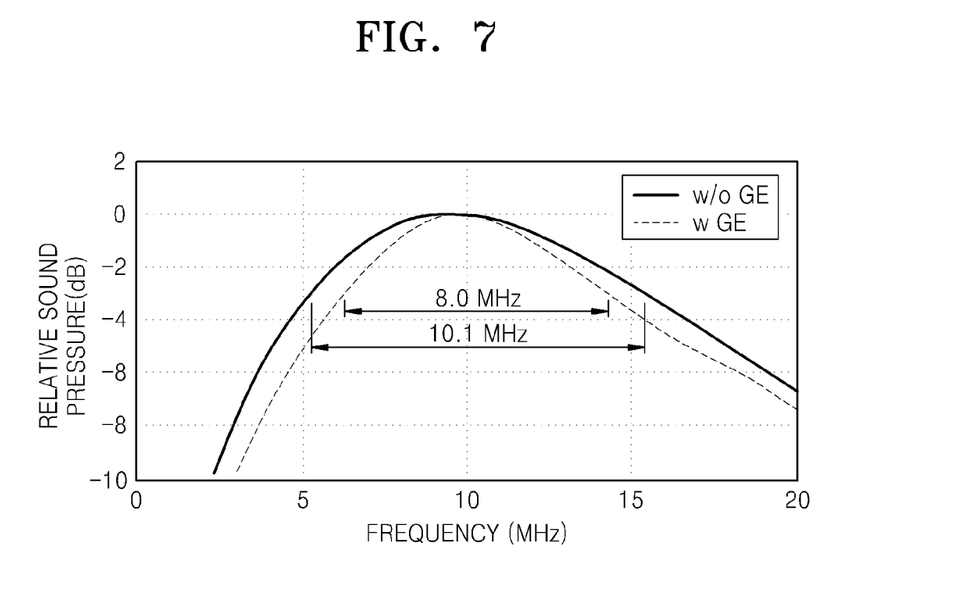
FIG. 7 is a graph showing simulation results of a bandwidth when a gap exists and when the gap does not exist, in a case where the ultrasonic cells are arranged as a square, according to a comparative example.

FIG. 7 is a graph showing a result of simulating bandwidths of a frequency response in a case where an effective gap GE (see FIG. 2) exists and a case where an effective gap GE does not exist when the ultrasonic cells 20 are in a square arrangement. A case where the effective gap GE does not exist denotes that the ultrasonic cells 20 located at edge portions of the adjacent first element 10-1 and second element 10-2 are separated from each other by a cell gap GC. A diameter of the ultrasonic cell 20 is 20 µm, the cell gap GC between the ultrasonic cells 20 is 5 µm, and a pitch PE between the elements is 15 µm.

Referring to FIG. 7, a frequency bandwidth when the gap GE exists may be narrower than that when the gap GE does not exist. The frequency bandwidth may further be reduced when the gap GE is increased. Thus, a method is necessary for reducing the effective gap GE between the first element 10-1 and the second element 10-2. That is, a gap between an ultrasonic cell 20a-1 (see FIG. 8) that is the closest to the second element 10-2 from among first ultrasonic cells 20a and an ultrasonic cell 20b-1 that is closest to the first element 10-1 from among second ultrasonic cells 20b, while maintaining the gap GM between the first ultrasonic cell 20a and the second ultrasonic cell 20b located at edge portions of the first element 10-1 and the second element 10-2.

Figure 8:
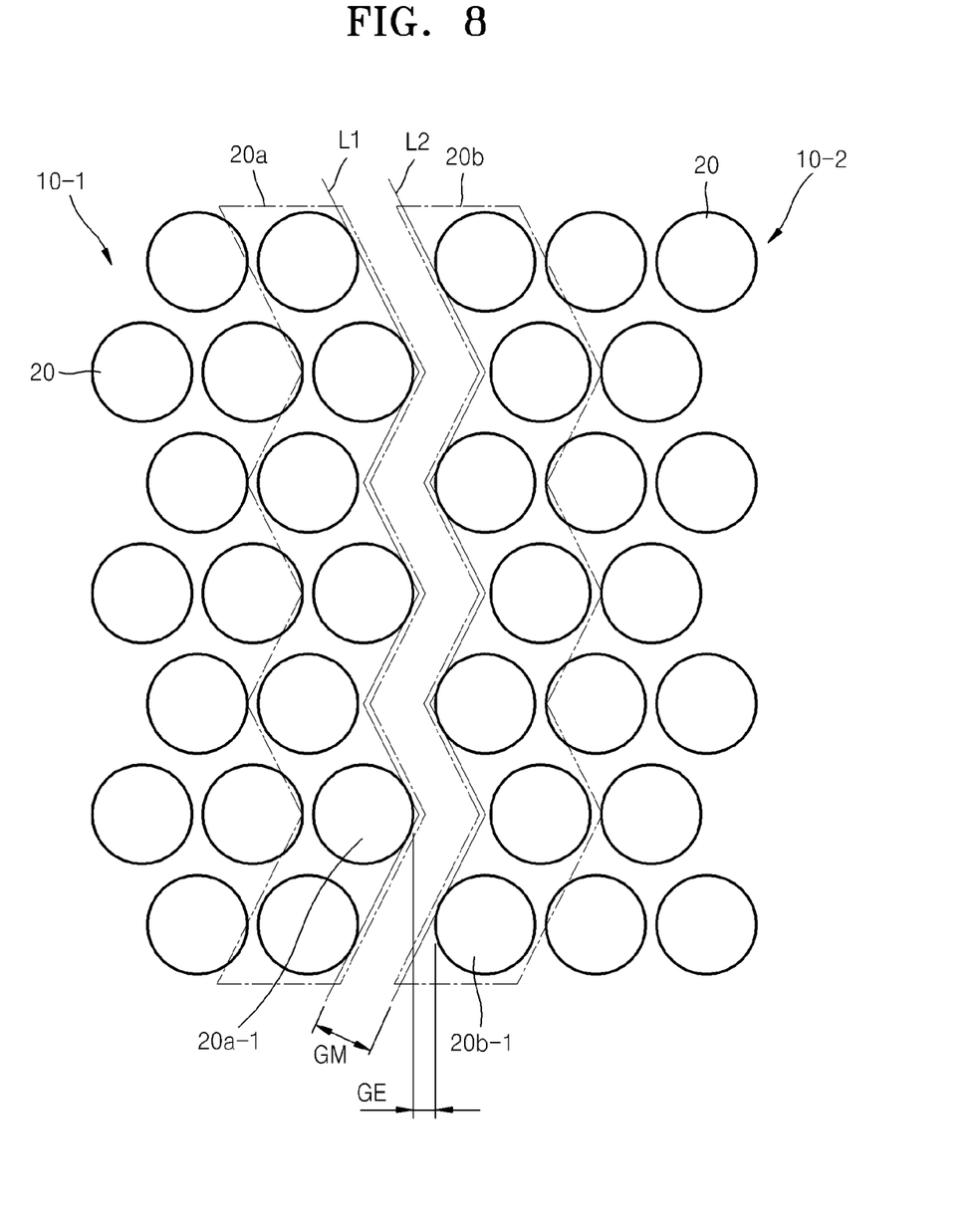
FIG. 8 is a plan view of a first element and a second element that are adjacent to each other in the ultrasonic transducer of FIG. 2.
Figure 9:
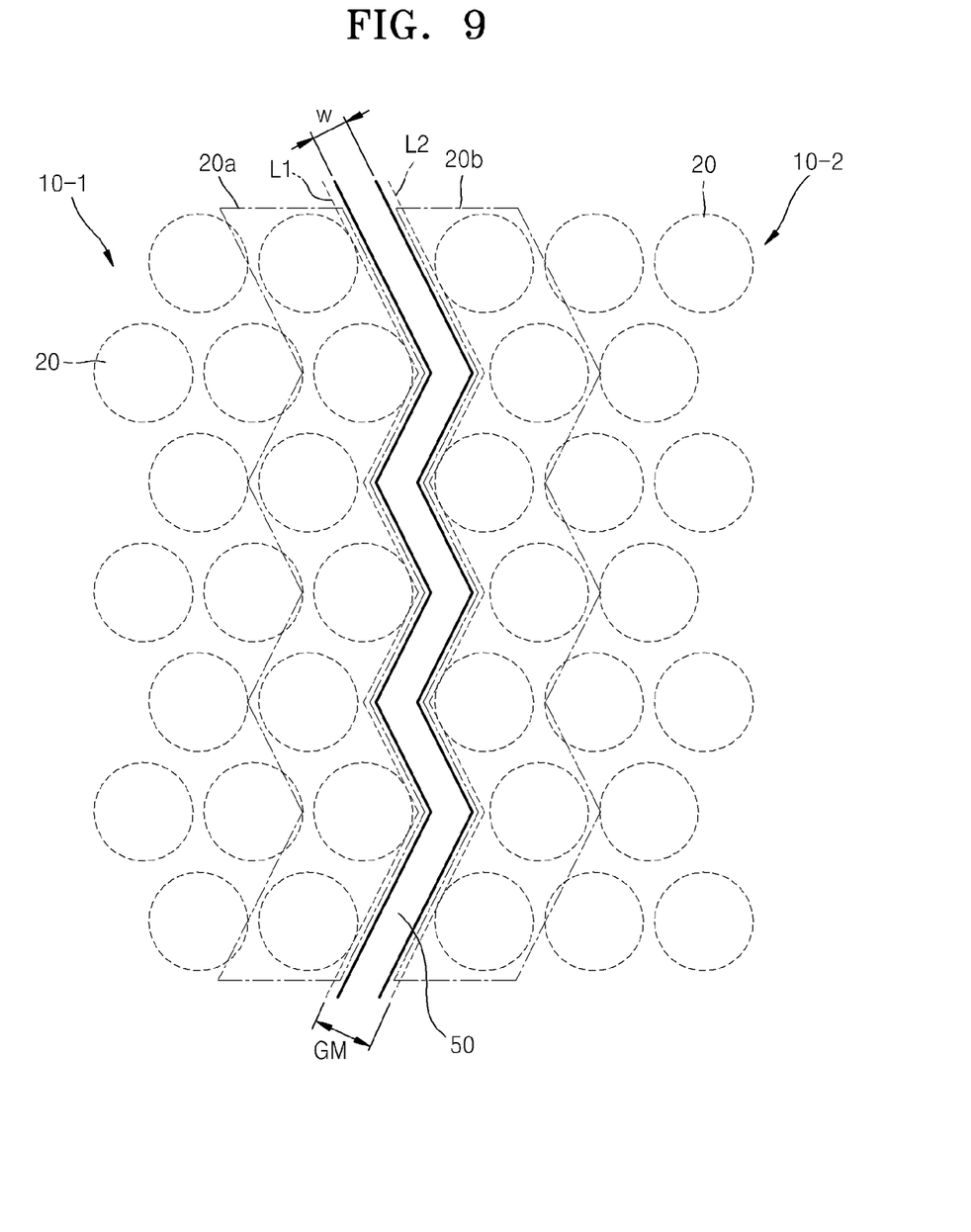
FIG. 9 is a diagram showing a trench formed on a lower surface of a substrate in the ultrasonic transducer of FIG. 8.

FIG. 8 is a plan view of the first element 10-1 and the second element 10-2 adjacent to each other in the ultrasonic transducer 5 shown in FIG. 2. FIG. 9 is a diagram showing a lower surface 21a of the substrate 21 in the ultrasonic transducer 5 of FIG. 8. Referring to FIG. 8, the ultrasonic cells 20 in the first element 10-1 and the second element 10-2 are hexagonally arranged. The first ultrasonic cells 20a located at an edge portion of the first element 10-1 are adjacent to the second ultrasonic cells 20b located at an edge portion of the second element 10-2. The first ultrasonic cells 20a and the second ultrasonic cells 20b located at the edge portions of the first element 10-1 and the second element 10-2 are arranged in a zig-zag pattern.

A first contour line L1 connects edges of the first ultrasonic cells 20a in the first element 10-1. Here, since each of the first ultrasonic cells 20a is circular, the first contour line L1 is a tangent connecting the edges of the first ultrasonic cells 20a. The first contour line L1 is formed as a zig-zag line that is repeatedly convex and concave toward the second element 10-2. A second contour line L2 connects edges of the second ultrasonic cells 20b of the second element 10-2. Here, since each of the second ultrasonic cells 20b is circular, the second contour line L2 is a tangent connecting the edges of the second ultrasonic cells 20b. The second contour line L2 is formed as a zig-zag line that is repeatedly convex and concave toward the first element 10-1.

In order to arrange the first element 10-1 and the second element 10-2 to be as close as possible, the first contour line L1 and the second contour line and L2 are complementary shaped. To do this, the ultrasonic cells 20 of the second element 10-2 are hexagonally arranged complementary with the ultrasonic cells 20 of the first element 10-1. As such, as shown in FIGS. 8 and 9, the first element 10-1 and the second element 10-2 may be arranged so that a perpendicular distance between the first contour lines L1 and the second contour line L2 may be equal to or greater than the width W of the trench 50.

Referring to FIG. 9, the trench 50 having the width W is provided in the substrate 21. The trench 50 may be formed between the first contour lines L1 and the second contour line L2 in a zig-zag pattern. The width W of the trench 50 is equal to or less than the gap GM. Therefore, the effective gap GE that is less than the gap GM, or the width W of the trench 50, may be formed between the first element 10-1 and the second element 10-2 while maintaining the gap GM in which the trench 50 may be formed.

The first ultrasonic cell 20a and the second ultrasonic cell 20b are arranged so as not to overlap with each other, and thus, the first element 10-1 and the second element 10-2, each forming an independent driving unit, do not overlap with each other. To do this, the effective gap GE between the ultrasonic cell 20a-1 (see FIG. 8) that is closest to the second element 10-2 from among the first ultrasonic cells 20a and the ultrasonic cell 20b-1 that is closest to the first element 10-1 from among the second ultrasonic cells 20b is greater than 0. The effective gap GE may be set to be equal to or greater than the cell gap GC in consideration of a resolution during the manufacturing processes.

Figure 10:
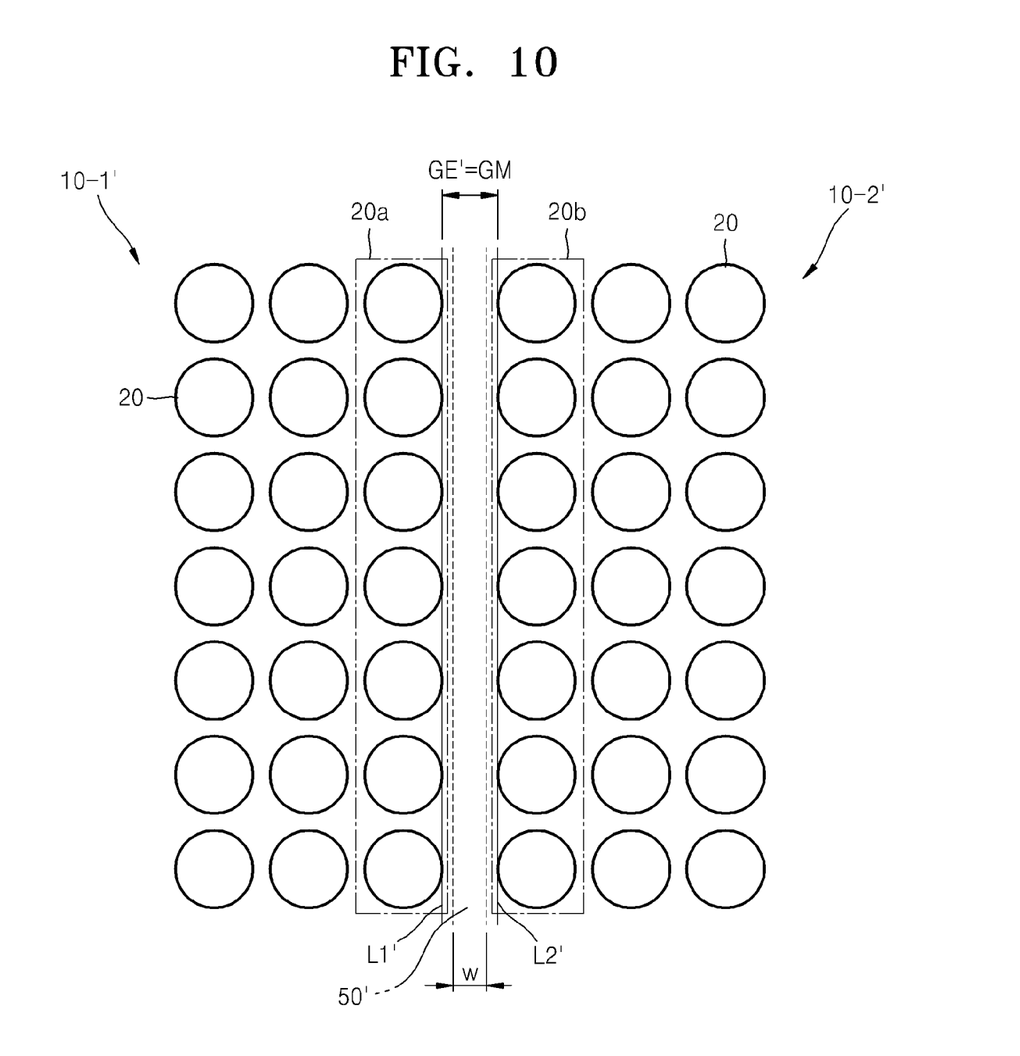
FIG. 10 is a plan view showing an effective gap in a case where the ultrasonic cells are arranged as a square in an element, according to a comparative example.

FIG. 10 is a plan view showing an effective gap GE' in a case of a square arrangement of the ultrasonic cells. Referring to FIG. 10, the ultrasonic cells 20 are arranged as squares in first element 10-1' and in second element 10-2'. Lines L1' and L2' connecting the edges of ultrasonic cells 20a' and 20b' located at edge portions of the first element 10-1' and the second element 10-2' are straight lines. In order to maintain a space where a trench 50' formed as a straight line having the width W, the lines L1' and L2' have to be separated from each other by as much as an effective gap GE'. Therefore, according to the square arrangement, the effective gap GE' between the first element 10-1 and the second element 10-2 is equal to or greater than the gap GM, or the width W of the trench 50'.

Figure 11:
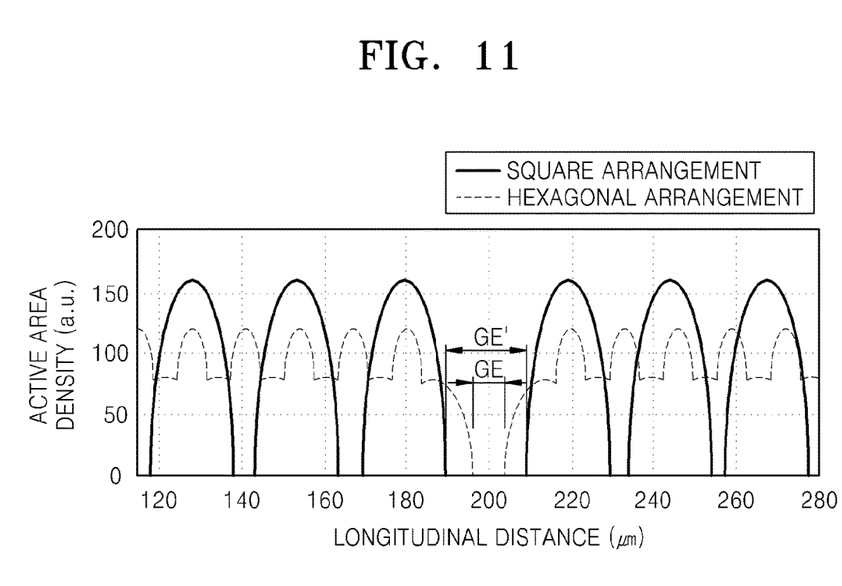
FIG. 11 is a graph for comparing effective area densities in the ultrasonic transducer of FIG. 8 according to the exemplary embodiment and in the ultrasonic transducer of FIG. 10 according to a comparative example.

FIG. 11 is a graph for comparing the effective area density in the ultrasonic transducer according to the exemplary embodiment as shown in FIG. 8 against that in an ultrasonic transducer according to the comparative example shown in FIG. 10. A diameter of the ultrasonic cell is 20 μm, the cell gap GC is 5 μm, and the element pitch PE is 15 μm. In the case of the square arrangement, three ultrasonic cells that are arranged in a transverse direction in an element are used to calculate the effective area density, and in the case of the hexagonal arrangement, three ultrasonic cells and two ultrasonic cells that are alternately arranged in the transverse direction are used.

Referring to FIG. 11, when compared against the ultrasonic transducer of the comparative example, the ultrasonic transducer 5 of the exemplary embodiment has a more uniform effective area, and the effective area of the ultrasonic cells 20 in the ultrasonic transducer 5 may be expanded. This denotes that the ultrasonic generation efficiency and the ultrasonic sensitivity may be improved. Also, the effective gap GE between the first element 10-1 and the second element 10-2 may be reduced to be less than the gap GM while maintaining the gap GM for forming the trench 50. Thus, a wide frequency response bandwidth may be obtained.

As described above, the first contour lines L1 and the second contour line L2 of the first element 10-1 and the second element 10-2 that are adjacent to each other are formed in a zig-zag pattern so as to be complementary with each other in the ultrasonic transducer 5, and a perpendicular distance between the first contour lines L1 and the second contour line L2 is equal to or greater than the width W of the trench 50 provided in the substrate 21.

In addition, the trench 50 is formed between the first contour line L1 and the second contour lines L2 in a zig-zag pattern. As such, the effective gap GE between the first element 10-1 and the second element 10-2 may be minimized while maintaining the gap GM for forming the trench 50, thereby increasing the effective area of the ultrasonic cells 20 in the ultrasonic transducer 5 and obtaining the wide frequency response bandwidth.

Also, in the first element 10-1 and the second element 10-2, each including the plurality of ultrasonic cells 20 that are hexagonally arranged, the first ultrasonic cells 20a located at the edge portion of the first element 10-1 and adjacent to the second element 10-2 and the second ultrasonic cells 20b located at the edge portion of the second element 10-2 and adjacent to the first element 10-1 may be arranged so as not to overlap with each other. Thus, the effective gap GE between the first element 10-1 and the second element 10-2 may be reduced, and at the same time, the gap GM for forming the trench 50 may be maintained between the first ultrasonic cells 20a and the second ultrasonic cells 20b.

Also, the first element 10-1 and the second element 10-2, including the plurality of cMUT cells that are arranged two-dimensionally on the upper surface 21a of the substrate 21 and that includes the trench 50 embedded from the lower surface 21b in a zag pattern, are arranged to be separated from each other while interposing the trench 50 therebetween. Also, the first ultrasonic cell 20a and the second ultrasonic cell 20b of the first element 10-1 and the second element 10-2 are arranged in a zig-zag pattern along the trench 50, thereby reducing the effective gap GE between the first element 10-1 and the second element 10-2.

In the above exemplary embodiments, the cMUT is adopted as the ultrasonic cell; however, the exemplary embodiments are not limited thereto. For example, if the pMUT is used as the ultrasonic cell, the same effects, that is, the increase in the effective area in the ultrasonic cells in the ultrasonic transducer and obtaining of the wide frequency response bandwidth, may be obtained.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An ultrasonic transducer comprising:
  a substrate including a trench formed in a lower surface of the substrate; and
  a first element and a second element formed on an upper surface of the substrate and are located adjacent to each other;
  wherein the trench is positioned between the first element and the second element,
  wherein each of the first element and the second element includes a plurality of ultrasonic cells that are two-dimensionally arranged,
  wherein each of a first contour line of the first element and a second contour line of the second element forms a zig-zag line respectively, the zig-zag lines being complementary with each other, the first contour line and the second contour line being adjacent to one another, and the trench is formed in a zig-zag pattern between the first contour line and the second contour line, and wherein a plurality of first ultrasonic cells adjacent to the trench among the plurality of ultrasonic cells in the first element and a plurality of second ultrasonic cells adjacent to the trench among the plurality of ultrasonic cells in the second element do not overlap with each other along an axis perpendicular to an overall length of the trench.

2. The ultrasonic transducer of claim 1, wherein the first contour line is a line configured to connect edges of the plurality of first ultrasonic cells, and the second contour line is a line connecting edges of the plurality of second ultrasonic cells.

3. The ultrasonic transducer of claim 2, further comprising an effective gap between a first ultrasonic cell located closest to the second element among the plurality of first ultrasonic cells and a second ultrasonic cell located closest to the first element among the plurality of second ultrasonic cells, and wherein a size of the effective gap is equal to or greater than a size of a cell gap between two adjacent ultrasonic cells of the plurality of ultrasonic cells in the first element and between two adjacent ultrasonic cells of the plurality of ultrasonic cells in the second element.

4. The ultrasonic transducer of claim 1, wherein the plurality of ultrasonic cells in the first element are hexagonally arranged, and the plurality of ultrasonic cells in the second element are hexagonally arranged with respect to the plurality of ultrasonic cells in the first element.

5. The ultrasonic transducer of claim 1, wherein each of the plurality of ultrasonic cells is a capacitive micromachined ultrasonic transducer (cMUT).

6. An ultrasonic transducer comprising:
a substrate;
a first element including a plurality of first ultrasonic cells hexagonally arranged on an upper surface of the substrate; and
a second element adjacent to the first element and including a plurality of second ultrasonic cells hexagonally arranged with respect to the first element,
wherein ultrasonic cells, among the plurality of first ultrasonic cells, that are located at a first edge portion of the first element are arranged in a first zig-zag pattern, and ultrasonic cells, among the plurality of second ultrasonic cells located at a second edge portion of the second element are arranged in a second zig-zag pattern complementary with the first zig-zag pattern, the second edge portion being adjacent to the first edge portion,
wherein a trench configured to block a transmission of a bulk acoustic wave between the first element and the second element is formed in the substrate, and
wherein the trench is formed in a zig-zag pattern between the plurality of first ultrasonic cells and the plurality of second ultrasonic cells.

7. The ultrasonic transducer of claim 6, wherein the trench is located on a lower surface of the substrate.

8. The ultrasonic transducer of claim 6, wherein an effective gap is located between a first ultrasonic cell located closest to the second element, among the plurality of first ultrasonic cells and a second ultrasonic cell located closest to the first element, among the plurality of second ultrasonic cells, and wherein a size of the effective gap is equal to or greater than a size of a cell gap between two adjacent ultrasonic cells among the plurality of first ultrasonic cells in the first element and between two adjacent ultrasonic cells among the plurality of second ultrasonic cells in the second element.

9. The ultrasonic transducer of claim 6, wherein each of the plurality of first ultrasonic cells and the plurality of second ultrasonic cells is a capacitive micromachined ultrasonic transducer (cMUT).

10. The ultrasonic transducer of claim 6, wherein the plurality of first ultrasonic cells and the plurality of second ultrasonic cells do not overlap with each other.

11. An ultrasonic diagnostic apparatus comprising:
an ultrasonic probe including an ultrasonic transducer comprising:
a substrate including a trench formed in a lower surface of the substrate,
a first element formed on an upper surface of the substrate including a plurality of first ultrasonic cells, and
a second element formed on the upper surface of the substrate adjacent to the first element including a plurality of second ultrasonic cells,
wherein the trench is positioned between the first element and the second element,
wherein a first contour line of the first element and a second contour line of the second element, each form a zig-zag line with respect to each other, the trench is formed in a zig-zag pattern between the first contour line and the second contour line, and first ultrasonic cells adjacent to the trench among the plurality of first ultrasonic cells in the first element and second ultrasonic cells adjacent to the trench among the plurality of second ultrasonic cells in the second element do not overlap with each other along an axis perpendicular to an overall length of the trench, and
wherein the ultrasonic probe is configured to transmit an ultrasonic wave toward an object and configured to receive an ultrasonic wave reflected by the object to generate an echo signal which includes information about the object; and
a signal processing device configured to generate images of the object based on the echo signal.

12. The ultrasonic diagnostic apparatus of claim 11, wherein the first contour line is a line connecting edges of the plurality of first ultrasonic cells adjacent to the trench, and the second contour line is a line connecting edges of the plurality of second ultrasonic cells adjacent to the trench.

13. The ultrasonic diagnostic apparatus of claim 12, wherein an effective gap is located between a first ultrasonic cell located closest to the second element among the plurality of first ultrasonic cells and a second ultrasonic cell located closest to the first element among the plurality of second ultrasonic cells, and wherein a size of the effective gap is equal to or greater than a size of a cell gap between two adjacent ultrasonic cells of the plurality of first ultrasonic cells and between two adjacent ultrasonic cells of the plurality of second ultrasonic cells.

14. The ultrasonic diagnostic apparatus of claim 11, wherein the plurality of first ultrasonic cells in the first element are hexagonally arranged, and the plurality of second ultrasonic cells in the second element are hexagonally arranged with respect to the plurality of first ultrasonic cells in the first element.

15. The ultrasonic diagnostic apparatus of claim 11, wherein each of the plurality of first ultrasonic cells and the plurality of second ultrasonic cells is a capacitive micromachined ultrasonic transducer (cMUT).

16. An ultrasonic transducer comprising:
   a substrate including a trench formed in a lower surface of the substrate;
   a first transducer element formed on an upper surface of the substrate and including a plurality of first ultrasonic cells; and
   a second transducer element formed on the upper surface of the substrate located adjacent to the first transducer element and including a plurality of second ultrasonic cells;
   wherein the plurality of first ultrasonic cells and the plurality of second ultrasonic cells are hexagonally arranged,
   wherein the trench is formed in a zig-zag pattern between the first transducer element and the second transducer element, and
   wherein first ultrasonic cells adjacent to the trench from among the plurality of first ultrasonic cells in the first transducer element and second ultrasonic cells adjacent to the trench among the plurality of second ultrasonic cells in the second transducer element do not overlap with each other along an axis perpendicular to an overall length of the trench.

17. The ultrasonic transducer according to claim 16, wherein each of the plurality of first ultrasonic cells and each of the plurality of second ultrasonic cells are a capacitive micromachined ultrasonic transducer (cMUT).

18. An ultrasonic diagnostic apparatus comprising:
   an ultrasonic probe including an ultrasonic transducer comprising:
      a substrate including a trench formed in a lower surface of the substrate,
      a first transducer element formed on an upper surface of the substrate and including a plurality of first ultrasonic cell, and
      a second transducer element formed on the upper surface of the substrate located adjacent to the first transducer element and including a plurality of second ultrasonic cells,
      wherein the plurality of first ultrasonic cells and the plurality of second ultrasonic cells are hexagonally arranged,
      wherein the trench is formed in a zig-zag pattern between the first transducer element and the second transducer element,
      wherein first ultrasonic cells adjacent to the trench among the plurality of first ultrasonic cells in the first transducer element and second ultrasonic cells adjacent to the trench among the plurality of second ultrasonic cells in the second transducer element do not overlap with each other along an axis perpendicular to an overall length of the trench, and
      wherein the ultrasonic probe is configured to transmit an ultrasonic wave toward an object and configured to receive an ultrasonic wave reflected by the object to generate an echo signal which includes information about the object; and
   a signal processing device configured to generate images of the object based on the echo signal.

* * * * *